(12) United States Patent
Qian

(10) Patent No.: US 10,226,048 B2
(45) Date of Patent: Mar. 12, 2019

(54) DISINFECTING DETERGENT

(71) Applicant: NANTONG SIRUI BIO-TECHNOLOGY CO., LTD, Jiangsu (CN)

(72) Inventor: Jianguo Qian, Jiangsu (CN)

(73) Assignee: NANTONG SIRUI BIO-TECHNOLOGY CO., LTD, Jiangsu (CN)

( * ) Notice: Subject to any disclaimer, the term of this patent is extended or adjusted under 35 U.S.C. 154(b) by 0 days.

(21) Appl. No.: 15/110,204

(22) PCT Filed: Jan. 5, 2015

(86) PCT No.: PCT/CN2015/070085
§ 371 (c)(1),
(2) Date: Jul. 7, 2016

(87) PCT Pub. No.: WO2015/103955
PCT Pub. Date: Jul. 16, 2015

(65) Prior Publication Data
US 2016/0330970 A1    Nov. 17, 2016

(30) Foreign Application Priority Data

Jan. 9, 2014    (CN) .......................... 2014 1 0010007

(51) Int. Cl.
| | | |
|---|---|---|
| *A01N 25/22* | (2006.01) | |
| *A01N 25/30* | (2006.01) | |
| *A01N 33/12* | (2006.01) | |
| *A01N 37/16* | (2006.01) | |
| *C11D 1/62* | (2006.01) | |
| *C11D 3/30* | (2006.01) | |
| *C11D 3/39* | (2006.01) | |
| *C11D 3/48* | (2006.01) | |
| *C11D 1/34* | (2006.01) | |
| *C11D 3/06* | (2006.01) | |
| *C11D 3/36* | (2006.01) | |
| *A01N 59/00* | (2006.01) | |
| *C11D 1/14* | (2006.01) | |
| *C11D 1/65* | (2006.01) | |

(52) U.S. Cl.
CPC ............ *A01N 59/00* (2013.01); *A01N 25/22* (2013.01); *A01N 25/30* (2013.01); *A01N 37/16* (2013.01); *C11D 1/146* (2013.01); *C11D 1/342* (2013.01); *C11D 1/62* (2013.01); *C11D 1/65* (2013.01); *C11D 3/06* (2013.01); *C11D 3/30* (2013.01); *C11D 3/361* (2013.01); *C11D 3/3942* (2013.01); *C11D 3/3945* (2013.01); *C11D 3/3947* (2013.01); *C11D 3/48* (2013.01); *C11D 1/143* (2013.01)

(58) Field of Classification Search
None
See application file for complete search history.

(56) References Cited

U.S. PATENT DOCUMENTS

| | | | | |
|---|---|---|---|---|
| 5,508,046 | A * | 4/1996 | Cosentino | A01N 59/00 424/616 |
| 5,900,256 | A * | 5/1999 | Scoville, Jr. | A01N 59/00 252/186.29 |
| 2004/0138084 | A1* | 7/2004 | Gohl | C11D 1/835 510/417 |
| 2005/0181965 | A1* | 8/2005 | Hsu | C11D 3/044 510/357 |
| 2006/0229225 | A1 | 10/2006 | Martin et al. | |
| 2009/0175956 | A1 | 7/2009 | Buschmann et al. | |
| 2009/0304608 | A1* | 12/2009 | Cueman | A61K 8/22 424/53 |
| 2009/0312292 | A1* | 12/2009 | Rovison | A01N 37/16 514/163 |
| 2011/0212933 | A1* | 9/2011 | Shapiro | A61K 31/045 514/171 |
| 2015/0291520 | A1* | 10/2015 | Reinold | C07C 407/00 562/6 |
| 2016/0330970 | A1 | 11/2016 | Qian | |

FOREIGN PATENT DOCUMENTS

| | | |
|---|---|---|
| CN | 101810171 | 8/2010 |
| CN | 102511478 | 6/2012 |
| CN | 102888304 | 1/2013 |
| CN | 103704264 | 4/2014 |

(Continued)

OTHER PUBLICATIONS

K Dancey. "Peracetic Acid a New Disinfection Approach." http://www.pncwa.org/assets/documents/2009%20PNCWA-%20Session%2015-1%20-%20Disinfection%20-%20Kelly%20Dancey.pdf, accessed by examiner Sep. 20, 2017, available online Sep. 17, 2009, 29 printed pages (Year: 2009).*

RJW Lambert, MD Johnston, E-A Simons. "A kinetic study of the effect of hydrogen peroxide and peracetic acid against *Staphylococcus aureus* and Pseudomonas aeruginosa using the Bioscreen disinfection method." Journal of Applied Microbiology, vol. 87, 1999, pp. 782-786. (Year: 1999).*

International Search Report dated Mar. 25, 2015 in corresponding International (PCT) Application No. PCT/CN2015/070085.

(Continued)

*Primary Examiner* — Isaac Shomer
(74) *Attorney, Agent, or Firm* — Wenderoth, Lind & Ponack, L.L.P.

(57) ABSTRACT

A disinfecting detergent comprising 0.1-6% (w/w %) of hydrogen peroxide, 0.01-0.6% (w/w %) of peracetic acid, 0.01-2% (w/w %) of an ion-pair reagent and/or a phase transfer catalyst, 0.01-1% (w/w %) of a surfactant, 0.1-3% (w/w %) of a base, 0-1% (w/w %) of a stabilizer, and 90-96% (w/w %) of water, where the pH value of the disinfecting detergent is 7.1-9.9. The disinfecting detergent has the advantages of low toxicity, low corrosivity, no pungent smell and fast, broad-spectrum and high-efficiency sterilization, virus killing effect and spore killing effect.

9 Claims, 2 Drawing Sheets

(56) References Cited

FOREIGN PATENT DOCUMENTS

| WO | WO-9949009 A1 | * | 9/1999 | ............. | C11D 3/361 |
| WO | WO-2014089633 A1 | * | 6/2014 | ............. | A01N 37/16 |

OTHER PUBLICATIONS

"Hydrogen Peroxide, Peracetic Acid and Sodium Percarbonate", Massachusetts Department of Environmental Protection, Oct. 2010, 17 pages.

Regulation (EU) No. 528/2012 concerning the making available on the market and use of biocidal products; Evaluation of active substances; Assessment Report—Peracetic acid, Nov. 2015.

Material Safety Data Sheet, Distilled Peracetic Acid, Texas Technology, Jun. 15, 2009, pp. 1-8.

Abstract of Yuan et al., "Kinetics of the peracetic acid decomposition: Part II: pH effect and alkaline hydrolysis", The Canadian Journal of Chemical Engineering, Wiley Online Library, Mar. 27, 2009.

Tetraacetylethylenediamine (TAED), (CAS 10543-57-4), Human & Environmental Risk Assessment on ingredients of European household cleaning products, Dec. 2002.

* cited by examiner

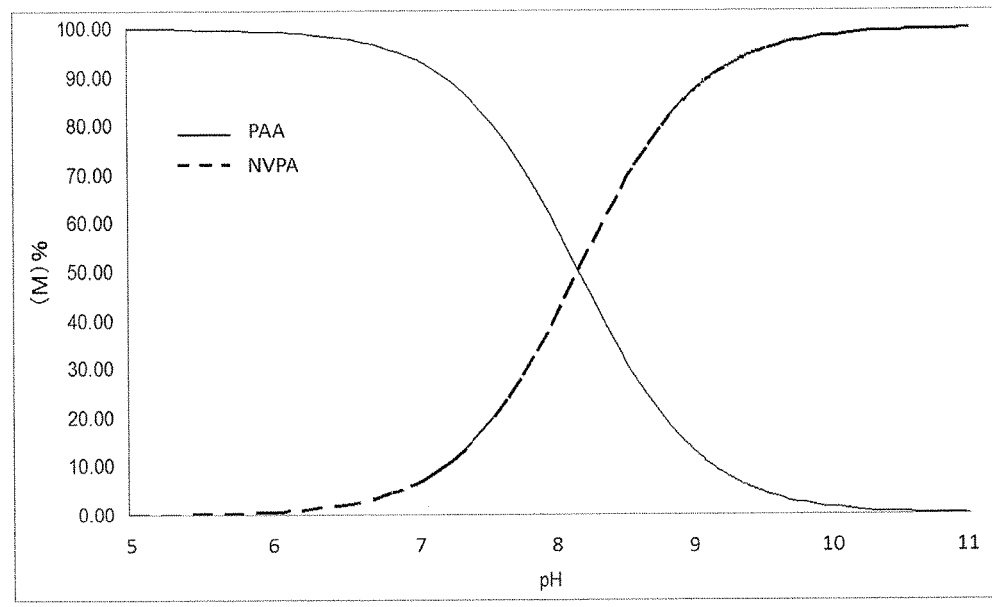
[Figure 1]
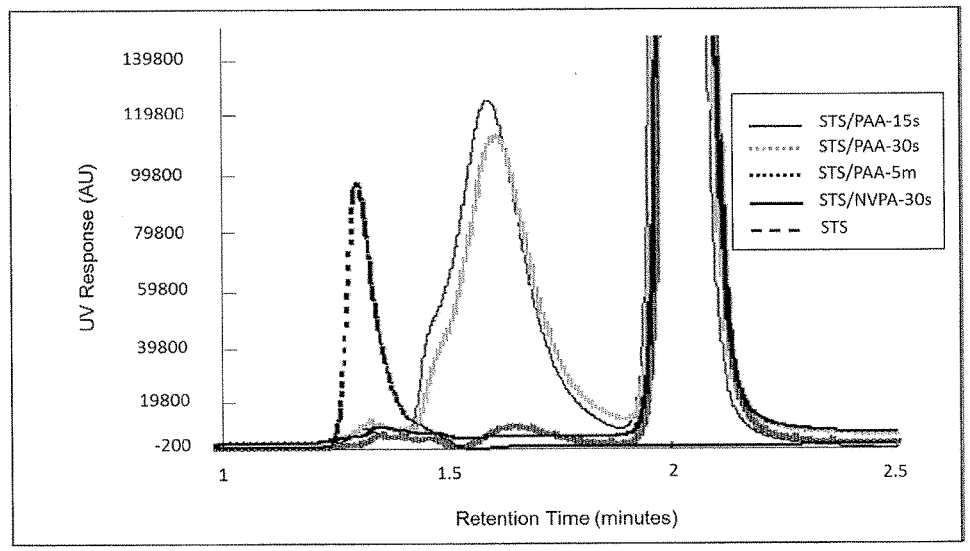
[Figure 2]

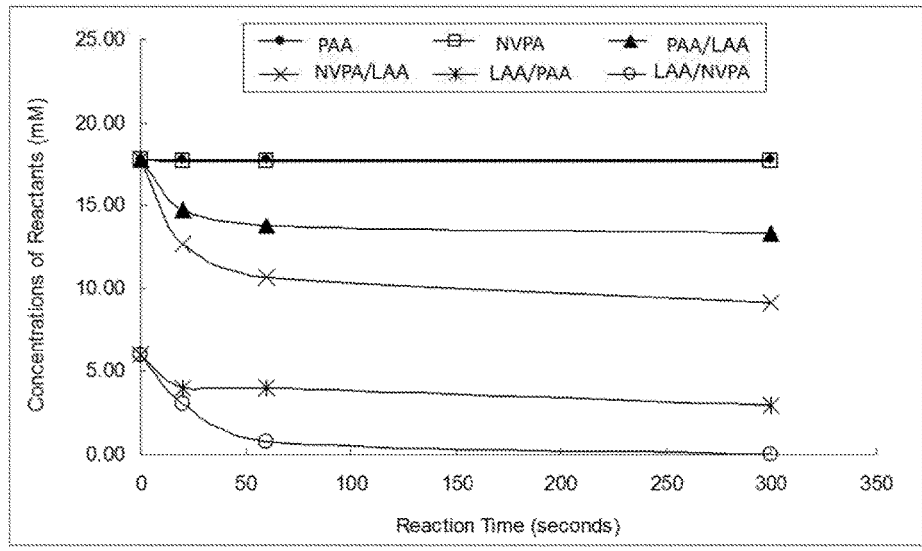
[Figure 3]
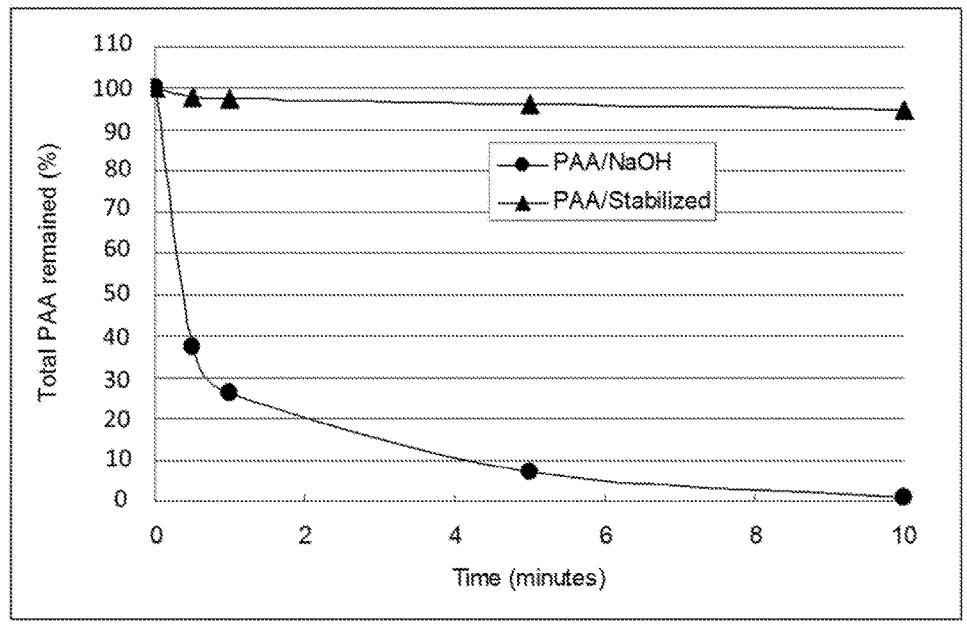
[Figure 4]

DISINFECTING DETERGENT

FIELD OF THE INVENTION

The present invention relates to a disinfecting detergent, which can be used as a disinfectant cleaner in family and public places.

BACKGROUND OF THE INVENTION

So far, no wide spectrum disinfection/sterilization cleaners have been used in public and family areas, with the exception of cleaners with powder type bleaches. The bleaches possess significant disadvantages: are very corrosive, which results in varying degrees of damage to the appliances and equipment in family and public places; generate chlorinated organic compounds when reacted with organic compounds in environment, some of which are highly toxic and probable human carcinogens; release strong pungent odor, which is harmful to human health, especially when applied in a large area, where the strong pungent smell is far beyond the range that people can bear.

A low concentration of hydrogen peroxide (HP) does not show strong and fast disinfecting efficacy, and cannot kill bacteria quickly with a high killing efficacy (Table 1); and high concentration HP is very hazardous in case of skin and eye contact, such that HP cannot be used as a disinfectant in common household and public place. Peracetic Acid (PAA) solution is not suitable to be used as a disinfectant cleaner in family and public place because it releases a very strong pungent odor.

TABLE 1

Test results of disinfecting efficacy by using of 2% HP.

| | E-Coli | | Staphylococcus Epidermidis | |
|---|---|---|---|---|
| | Contact time | | | |
| | 1 minute | 2 minutes | 1 minute | 2 minutes |
| Disinfecting efficacy | ~90% | ~99% | ~90% | ~99% |

Based on the above, it is necessary to develop a low corrosive, non-toxic disinfectant cleaner, with less or no pungent odor, that can kill bacteria, viruses and spores quickly. Such a disinfectant cleaner can be used in the possible outbreak of plague and influenza, as well as heavy disaster places for large area disinfection to stop the outbreaks and spread of plague and influenza. Since such a disinfectant cleaner is not toxic and has no strong pungent odor, it will not affect the health of rescue workers or rescue personnel.

SUMMARY OF THE INVENTION

This invention is a disinfecting detergent with low toxicity, less corrosion and no strong pungent odor. The disinfecting actives are HP and conjugate base of PAA, i.e., the corresponding anion. In the basic solution, where pH is between 7.1 and 9.9, typically between 9.0 and 9.5, PAA is converted into a stronger oxidizing metastable anion (table II), i.e., non-volatile peracetate (NVPA) in the following reaction (1), which has fast disinfection ability. Since NVPA is non-volatile, the strong pungent odor from PAA will be eliminated or decreased.

PAA is a weak organic acid in aqueous solution with a pKa=8.2 (Reaction 1).

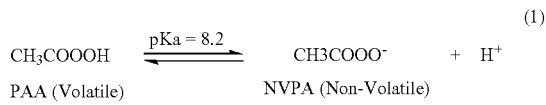

(1)

As pH of the solution increases, PAA concentration decreases, and NVPA concentration increases (FIG. 1).

The concentrations of PAA and NVPA are equal when the pH is at 8.2. As pH increases to 9.5, only 5% of initial PAA concentration exists in an aqueous solution, and 95% exists in the state of NVPA. This significant decrease in the concentration of peracetic acid results in the elimination or significant minimization of the pungent odor due to the volatilization of peracetic acid.

Tests of Oxidization Ability and Disinfecting Efficacy:

These tests were performed to understand whether or not the oxidation and disinfecting abilities decreased when PAA was converted to NVPA. This is a key of the invention.

Oxidization Ability:

Experimental results indicated that PAA showed greater oxidation ability against sodium thiosulfate (STS) in the basic solution than in acidic solution (FIG. 2).

The test results indicated that PAA in basic solution oxidized STS completely in 30 seconds, which consumed over 75% PAA. The stoichiometry indicated that complete oxidation of STS was mainly due to NVPA and less than 10% STS was oxidized by HP. However, in the acidic solution, STS was first oxidized to a reducing intermediate (FIG. 2, RT=1.6 minutes), which can be further oxidized by PAA and HP. The complete oxidation of the intermediate took about 5 minutes. During the complete oxidation reaction, less than 50% PAA was consumed to oxidize STS and its degradation intermediate, and other STS and the intermediate were oxidized by HP. The stoichiometry indicated that greater than 30% STS and the intermediate were oxidized by HP. These experimental results indicated that PAA in basic solution showed greater oxidation ability than in the acidic solution. The oxidization test results of sodium sulfite (SS) indicated that complete oxidization of SS took less than 30 seconds in the basic solution, and about 90% SS was oxidized by NVPA and 10% STS was oxidized by HP. However, the complete oxidization of SS took slightly more than 30 seconds in the acidic solution, and about 30% SS was oxidized by PAA and about 70% SS was oxidized by HP. These test results demonstrate that NVPA provides greater oxidization ability than PAA.

L-ascorbic acid (LAA) test results also showed that PAA in the basic solution had greater oxidation ability than in the acidic solution (FIG. 3). In the basic solution, the complete oxidation of LAA took 5 minutes, and in the acidic solution, only 50% LAA was oxidized. In both reactions, the HP concentration remained constant, which indicated that the oxidization of LAA was mainly due to NVPA or PAA.

Disinfecting Efficacy:

Test results indicate that the disinfecting detergent can kill bacteria, virus and spores quickly (Table 2).

TABLE

Disinfecting efficacy tests. The contact time was between 1 and 3 minutes.

| | Microorganisms | Killing Efficacy |
|---|---|---|
| Vegetative Cell | Escherichia Coli | >99.9999* |
| | Staphylococcus Aureus | >99.9999* |
| Virus | Poliovirus | >99.99* |
| | Influenza H1N1 | >99.999* |
| Spore | Bacillus Subtilis | >99.999* |
| | A. Flavus Spore | >99.9999* |

*No survivors (number represents limit of detection).

Stabilization of NVPA:

PAA is not very stable in both acidic and basic solutions (reactions 2 and 3), and is decomposed into acetic acid and oxygen easily. Additionally, PAA is decomposed by metal catalysis and hydrolysis, respectively, in an aqueous solution. As the pH of the solution increases, the hydrolysis decomposition rate of the PAA will increase significantly. When sodium hydroxide was used to adjust the pH of PAA solution to 9.3, about 80% of the total PAA were decomposed in 1 minute, with more than 90% being decomposed in 5 minutes. (FIG. 4).

(2)

(3)

Rapid decomposition of PAA will result in a loss of the disinfecting ability. Thus, it is critical to maintain PAA relatively stable in an alkaline solution. When pH was adjusted partially by sodium carbonate, greater than 90% of the total PAA was maintained in the 10 minutes (FIG. 4). The addition of a metal complexing agent, such as sodium pyrophosphate, etc., may be used to stabilize PAA. It is very important to maintain a relatively long pot-life of NVPA, because some microorganisms are difficult to being killed. Such microorganisms may require at least 3-5-minutes of contact time with the disinfecting detergent. Since NVPA is not very stable, the formulation of the invention is divided to two parts to preserve a long shelf life of PAA. The two parts will be mixed just prior to use. After mixing, PAA will be converted to NVPA and 90% of the total PAA will remain for at least 10 minutes.

Ion Pair Reagent and Phase Transfer Catalyst:

The Ion pair reagent and/or phase transfer catalyst may be a quaternary ammonium compounds, such as tetrabutylammonium hydroxide. In the environment, or in practice, the microorganisms are always likely to be surrounded by contaminants, and some of which are not water soluble, which makes it difficult for aqueous disinfectants to quickly penetrate the hydrophobic contaminants to kill the microorganisms. If ion-pairing reagents and peracetic acid anion form hydrophilic ion pair intermediates (Reaction 4), NVPA will be relatively easy to penetrate the contaminants to reach the surface of the microorganisms, and will assist NVPA in penetrating the outer protective layer of certain microorganisms, thereby killing them.

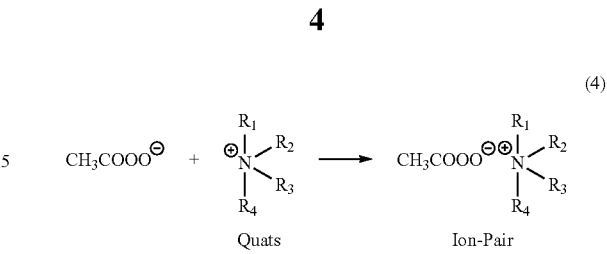

(4)

A Composition of the Disinfecting Detergent Comprises:
Disinfecting actives: Hydrogen peroxide, 0.1-6% (w/w %);
Peracetic acid, 0.01-0.6% (w/w %);
Ion-pair reagent and phase transfer catalyst: 0.01-2% (w/w %);
Surfactant: 0.01-1% (w/w %);
Bases: 0.1-3% (w/w %);
Stabilizers: 0-1% (w/w %); and
Water: 90-96% (w/w %),
where the pH of the formulation is between 7.1 and 9.9, typically between 9 and 9.5.

An important improvement achieved by Applicant is to convert PAA and HP to the high oxidizing metastable anions in the basic solution, which have fast disinfecting ability, and converts most of the PAA to non-volatile peracetate (NVPA), thus decreasing or eliminating the strong pungent odor due to PAA.

A further improvement achieved by Applicant is to use tetrabutylammonium hydroxide (TBAH), cetyltrimethylammonium bromide (CTAB), or a mixture of both as ion pair and phase transfer catalyst reagents, which assist the disinfecting actives in contacting the microorganisms that are covered by organic contaminants in the environment.

A further improvement achieved by Applicant is to use a phosphonate surfactant, a sulfonate surfactant, or mixtures thereof. The phosphonate surfactants may be 1-hydroxyethylidene-1,1,-diphosphonic acid (HEDPA) or Dextrol™ OC-40 Phosphate Ester. The sulfonate surfactants may be sodium dodecyl sulfate (SDS) or dodecyl amine sulfonate.

A further improvement achieved by Applicant is to use bases to convert PAA and HP to corresponding anions. These bases may be sodium carbonate, sodium hydroxide, sodium phosphate, an organic base such as TBAH, benzylamine or ammonium hydroxide.

A further improvement achieved by Applicant is to use metal complexing agents to stabilize PAA and NVPA. The complexing agents may be 8-hydroxyquinoline, sodium pyrophosphate, HEDPA or ethylene diamine tetraacetate (EDTA). Sodium carbonate can also be used to stabilize NVPA.

The disinfecting detergent of the present invention has low toxicity, low causticity, and less pungent odor. Additionally, the disinfecting detergent can be used in public and family places, and various types of stations, such as airport lounges, hospitals, and restaurants and for family health. The disinfecting detergent is especially suitable for large area spray for influenza and plague areas, to kill bacteria, viruses and spores quickly, thus significantly reducing influenza and plague outbreak and spread.

DESCRIPTION OF THE FIGURES

FIG. 1. The dissociation rate and concentration of PAA in aqueous solution changes with pH of the aqueous solution. PAA means peracetic acid, and NVPA means peracetic acid anion.

FIG. 2. Relation between degradation time and degradation rates of sodium thiosulfate and its degradation products. The concentrations of PAA and HP were 17.4 and 64.8 mM respectively, the concentration of sodium thiosulfate was 5.0 mM, the pH of PAA solution was 2, and the pH of NVPA solution was 9.3.

FIG. 3. Reaction of L-ascorbic Acid (LAA) with 6.0 mM, HP with 64.8 mM, and PAA with 47.8 mM in an aqueous solution. The pH of the acidic solution was 2.3. The pH of the alkaline solution was 9.4.

FIG. 4. The pH of PAA solution was 9.3. The initial concentrations of PAA and HP were 0.2% (w/w %) and 4% (w/w %), respectively. The pH of the solution was adjusted by sodium hydroxide solution or sodium phosphate solution, and sodium carbonate or a stabilizer such like sodium pyrophosphate was used to stabilize PAA. The quantitative determination of PAA/NVPA was performed by ion-exchange chromatography.

DETAILED DESCRIPTION OF THE INVENTION

The following description of embodiments is merely exemplary in nature and is in no way intended to limit the scope of invention.

A disinfecting detergent includes the following components:
Disinfecting actives: Hydrogen peroxide: 0.1-6% (w/w %), Peracetic acid: 0.01-0.6% (w/w %);
Ion pair reagent and/or phase transfer catalyst: 0.01-2% (w/w %);
Surfactant: 0.01%-1% (w/w %);
Base: 0.1-3% (w/w %);
Stabilizer: 0-1% (w/w %); and
Water: 90-96% (w/w %).

The pH of the disinfecting detergent is between 7.1 and 9.9, and typically between 9 and 9.5 for normal use.

Under alkaline conditions (pH value of 7.1-9.9, the best use of pH between 9-9.5), hydrogen peroxide and peracetic acid will be converted to high oxidizing metastable anions, which have fast disinfecting ability and make PAA become non-volatile peracetate (NVPA), thus decreasing or eliminating the strong pungent odor due to PAA.

The ion pair reagent and phase transfer catalyst may be TBAH and CTAB or a mixture thereof, which will help disinfecting actives to contact to the microorganisms in a complex application environment to kill them quickly. Surfactants include a sulfonate surfactants, phosphonate surfactants, and mixtures thereof. The phosphonate surfactants may be HEDPA and Dextrol™ OC-40 Phosphate Ester. The sulfonate surfactants may be SDS and ammonium lauryl sulfonate.

Bases may be sodium hydroxide, sodium carbonate, sodium phosphate and organic bases, such as TBAH, benzylamine or ammonium hydroxide. These compounds will react with hydrogen peroxide and peracetic acid to form the corresponding anions.

Stabilizers may be metal complexing agents, such as 8-hydroxyquinoline, sodium pyrophosphate, HEDPA and EDTA. The test results indicate that sodium carbonate can also play an important role in stabilizing peracetic acid anion.

The components of the disinfecting detergent include two groups called Part A and Part B.

Part A comprises: disinfecting actives: hydrogen peroxide, 0.1-10% (w/w %); peracetic acid, 0.01-0.8% (w/w %); a metal complexing agent: HEDPA and sodium pyrophosphate, 0.01-1% (w/w %); and water: 90-94% (w/w %).

Part B comprises: ion pair reagents and phase transfer reagent, 0.01-2% (w/w %); surfactants, 0.01-1% (w/w %); bases 0.1-3% (w/w %); and water: 90-96% (w/w %).

The pH of the disinfecting detergent is between 7.0 and 9.9, and typically, between 9 and 9.5.

A non-limiting embodiment is as follows. Disinfection active is hydrogen peroxide and peracetic acid; ion pair reagent and a phase transfer reagent is tetrabutylammonium hydroxide (TBAH) or cetyl trimethyl ammonium bromide; surfactant sodium dodecyl sulfonate (SDS) or 1-hydroxyethylidene-1,1,-diphosphonic acid (HEDPA); the base is an inorganic base, such as sodium hydroxide, ammonium hydroxide, sodium carbonate, sodium phosphate, and organic bases, such as tetrabutyl ammonium, benzylamine; and stabilizers are pyrophosphate, 1-Htdroxyethylidene-1, 1-diphosphonic acid (HEDPA).

Preparation examples of disinfectant cleaners are described in the following tables.

TABLE 3

Preparation examples of disinfectant cleaners
Formulation 1 of disinfectant cleaner

| | Part A | | | | Part B | | | |
|---|---|---|---|---|---|---|---|---|
| | PAA (%) | HP (%) | SPP (%) | Water (%) | NaOH (%) | TBAH (%) | SDS (%) | Water (%) |
| Conc in Part A or Part B (%) | 0.45 | 8.0 | 0.20 | >91 | 0.60 | 1.00 | 0.10 | >98 |
| Conc in mixed (%) | 0.225 | 4.0 | 0.10 | | 0.30 | 0.50 | 0.05 | >94 |

TABLE 4

Preparation examples of disinfectant cleaners
Formulation 2 of disinfectant cleaner

| | Part A | | | | Part B | | | |
|---|---|---|---|---|---|---|---|---|
| | PAA (%) | HP (%) | HEDP (%) | Water (%) | Na$_2$CO$_3$ (%) | TBAH (%) | CTAB (%) | Water (%) |
| Conc in Part A or Part B (%) | 0.70 | 5.00 | 0.20 | >94 | 0.88 | 1.00 | 0.20 | >97 |
| Conc in mixed (%) | 0.35 | 2.50 | 0.10 | | 0.44 | 0.50 | 0.10 | >95 |

Based on scientific studies, the disinfecting detergent uses hydrogen peroxide, peracetic acid, ion pair/phase transfer catalyst reagents (quats) and water, etc., to kill bacteria, viruses and spores quickly. Since the broad-spectrum disinfectant cleaners have low causticity, low toxicity, non-irritating odor, low residues and other good environmental features, they may be used in a variety of public places and households, and various types of stations, such as bus/train stations, airport lounges, hospitals, restaurants and family health. The disinfecting detergent is especially suitable for large area spray in the Influenza, plague area to kill bacteria, virus and spores quickly, which can reduce influenza and plague outbreak and spread significantly.

The invention claimed is:

1. A disinfecting detergent composition comprising:
    0.1%-6% (w/w %) of hydrogen peroxide (HP) and 0.01%-0.6% (w/w %) of peracetic acid (PAA) as disinfecting actives,
    0.01%-2% (w/w %) of an ion-pair reagent and/or a phase transfer catalyst,
    0.01%-1% (w/w %) of a surfactant,
    0.1%-3% (w/w %) of a base, wherein the base comprises sodium carbonate and another compound selected from the group consisting of sodium hydroxide, sodium phosphate, tetrabutyl ammonium hydroxide, benzylamine and ammonium hydroxide,
    0-1% (w/w %) of a stabilizer, and
    90%-96% (w/w %) of water,
    wherein the pH of the composition is 8.2-9.9.

2. The composition of claim 1, wherein said disinfecting detergent is characterized in converting hydrogen peroxide and peracetic acid to high oxidizing metastable anions, which have fast disinfecting ability and make PAA become non-volatile peracetate (NVPA), thus eliminating the strong pungent odor due to PAA.

3. The composition of claim 1, wherein the ion-pair reagent and/or phase transfer catalyst is tetrabutylammonium hydroxide (TBAH), cetyltrimethylammonium bromide (CTAB), or a mixture thereof.

4. The composition of claim 1, wherein the surfactant is a mixture of at least one selected from the group consisting of sulfonate surfactants and phosphonate surfactants.

5. The composition of claim 1, wherein the stabilizer is a metal complexing agent selected from the group consisting of 8-hydroxyquinoline, sodium pyrophosphate, 1-Hydroxyethylidene-1, 1,-diphosphonic acid (HEDPA), and ethylene diamine tetraacetate (EDTA).

6. The composition of claim 4, wherein the phosphonate surfactant is selected from the group consisting of 1-Hydroxyethylidene-1,1,-diphosphonic acid (HEDPA) and the free acid form of a tridecyl alcohol ethoxylated phosphate ester.

7. The composition of claim 4, wherein the sulfonate surfactant is selected from the group consisting of sodium dodecyl sulfate (SDS) and dodecyl amine sulfonate.

8. The composition of claim 1, wherein said pH of the composition is 9.0-9.5.

9. A method of disinfecting, comprising applying the composition of claim 1 to a surface or area in need of disinfecting.

* * * * *